United States Patent [19]
Karkar

[11] Patent Number: 4,911,549
[45] Date of Patent: Mar. 27, 1990

[54] HEPARIN MONITORING SYSTEM AND METHODOLOGY

[75] Inventor: Maurice N. Karkar, Costa Mesa, Calif.

[73] Assignee: Baxter International Inc., Deerfield, Ill.

[21] Appl. No.: 177,306

[22] Filed: Apr. 5, 1988

[51] Int. Cl.$^4$ .................... G01N 33/487; G01N 21/31
[52] U.S. Cl. ...................................... 356/39; 128/633; 356/407; 356/414
[58] Field of Search ...................... 356/39, 40, 41, 407, 356/409, 414, 320; 128/633

[56] References Cited

U.S. PATENT DOCUMENTS

| | | | |
|---|---|---|---|
| 3,910,701 | 10/1975 | Henderson et al. | 356/39 |
| 4,195,932 | 4/1980 | Popelka | 356/407 |

OTHER PUBLICATIONS

Grant et al, "Metachromatic Activity of Heparin and Heparin Fragments" Analytical Biochemistry, vol. 137, pp. 25–31, 1983.
Jacques, "Detection of Heparin and Related Sulfated Mucopolysaccharides", Method of Biochemical Analysis, vol. 24, pp. 238–241, 1977.
Jacques et al., "A Modified Method for the Colormetric Determination of Heparin", Canadian Journal of Physiology & Pharacology, vol. 45, pp. 789–794, 1967.
Gundry et al., "Clinical Evaluation of a New Rapid Heparin Assay Using the Dye Azurea", American Journal of Surgery, vol. 148, pp. 191–193, 1984.
Klein, "A Colorimetric Assay for Chemical Heparin in Plasma", Analytical Biochemistry, vol. 1241, pp. 59–64, 1982.
Durove et al, "Instrument for Measuring Microconcentrations of Indicator Dyes in Blood", Biomed. Eng. (U.S.A.), vol. 12, #1, Jan.–Feb. 1978, pp. 20–22.

*Primary Examiner*—Vincent P. McGraw
*Attorney, Agent, or Firm*—Michael C. Schiffer; Loyal M. Hanson

[57] ABSTRACT

A system for measuring heparin concentration in a sample of blood plasma includes a vessel for containing a sample of blood plasma to which a dye such as azure A has been added, and a light source for transmitting light at each of two different wavelengths through the sample while the sample is in the vessel, one of which wavelengths may be relatively insensitive to heparin dilution. A detector arrangement detects the light at each of the two different wavelengths that is transmitted through the sample to produce two different signals, each one of which signals is indicative of the light transmitted through the sample at a respective one of the two different wavelengths. Processing components process the two different signals to produce an output signal indicative of the amount of heparin concentration that compensates for the effect of plasma dilution by comparing the two signals.

13 Claims, 5 Drawing Sheets

HEPARIN MONITORING SYSTEM AND METHODOLOGY

BACKGROUND OF THE INVENTION

1. Technical Field

This invention relates generally to metachromatic measurement of heparin concentration, and more particularly to a new and improved method of assaying heparin in plasma with azure A.

2. Background Information

Heparin is an anticoagulant that is used in many applications such as in surgery of the heart and blood vessels, with organ transplants and artificial organs, for cardiovascular diagostic techniques, and for the control and prevention of thromboembolism following surgical operations. In this regard, it may be desirable to measure the heparin concentration in the patient in order to control the level of heparin and protamine (which is used to neutralize heparin). Failure to do so may result in a level that leads to hemorrhage and other clinical complications.

One method of colorimetric assay for plasma heparin propounded by M.D. Klein, et al. in a publication entitled "A colorimetric Assay for Chemical Heparin in Plasma", Analytical Biochemistry 1241, 59-64 (1982), employs the metachromasia of azure A when heparin is added. According to this method, heparin concentration is obtained from light absorbance measurements at a wavelength of six hundred twenty nanometers.

Although effective in some respects, it is found that measurements taken in this manner are inaccurate with diluted blood plasma, e.g. plasma containing saline. Thus, it is desirable to have a new and improved method that overcomes this concern while retaining the speed and simplicity of azure A assaying.

SUMMARY OF THE INVENTION

This invention recognizes the above mentioned inaccuracies, identifies the causes, and provides a new and improved system and method that reduces the inaccuracy in prior art methods of azure A assaying.

Briefly, the above and further objects of the present invention are realized by taking light transmittance measurements at each of at least two different wavelengths, one of which is relatively insensitive to heparin dilution, and then comparing the measurements to neutralize the effect of plasma dilution. Thus, the invention overcomes various concerns of the prior art by identifying and using a second, relatively dilution-insensitive wavelength.

Generally, a system constructed according to the invention for measuring heparin concentration in a sample of blood plasma to which a dye, such as azure A, has been added, includes a vessel for containing the sample and a light source for transmitting light at each of two different wavelengths through the sample while it is in the vessel. This may take the form of light emitting diodes operational connected t suitable circuitry and properly positioned proximate an optical cuvette.

The system includes a detector for detecting the light at each of the two different wavelengths that is transmitted through the sample to produce two different signals, each one of which signals is indicative of the light transmitted through the sample at a respective one of the two different wavelengths. This may be accomplished with photodetectors.

Electrical circuitry is employed to process the two different signals to produce an output signal indicative of the amount of heparin concentration that compensates for the effect of plasma dilution by comparing the two signals.

According to one aspect of the invention, the second one of the two wavelengths is chosen so that the amount of light of the second wavelength that is transmitted through the sample is substantially less dependent upon heparin concentration than is the amount of light of the first wavelength that is transmitted through the sample. For this purpose, the first wavelength may be in the range of about 610 nanometers to about 640 nanometers, and the second wavelength in the range of about 520 nanometers to about 560 nanometers.

According to another aspect of the invention, the second one of the two wavelengths is chosen so that the amount of light of the second wavelength that is transmitted through the sample decreases with increasing heparin concentration. For this purpose, the first wavelength may be in the range of about 610 nanometers to about 640 nanometers, and the second wavelength in the range of about 520 nanometers to about 540 nanometers.

The method of measuring heparin concentration in a sample of blood plasma proceeds by containing a sample of blood plasma to which a dye has been added, and transmitting light at each of two different wavelengths through the sample. Then, light transmitted through the sample at each of the two different wavelengths is detected to produce two different signals, each one of which signals is indicative of the light transmitted through the sample at a respective one of the two wavelengths. The two different signals are processed to produce an output signal indicative of the amount of heparin concentration that compensates for the effect of plasma dilution.

The above mentioned and other objects and features of this invention and the manner of attaining them will become apparent, and the invention itself will be best understood, by reference to the following description taken in conjunction with the accompanying illustrative drawings.

DESCRIPTION OF THE PREFERRED EMBODIMENTS

Figure 1:
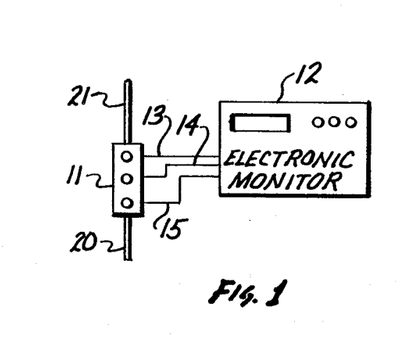
FIG. 1 is a diagrammatic view f an optical cuvette and electronic monitor utilized to measure heparin concentration in a sample of blood plasma according to the method of the invention.
Figure 2:
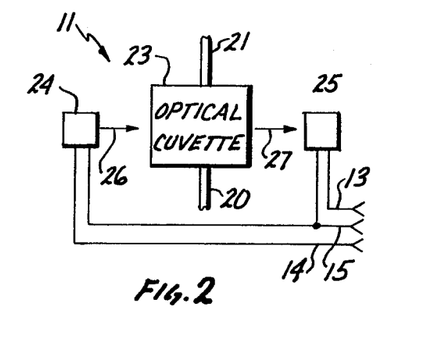
FIG. 2 is a diagrammatic view of a system utilizing the optical cuvette according to the invention for monitoring heparin concentration during extracorporeal bypass surgery.
Figure 3:
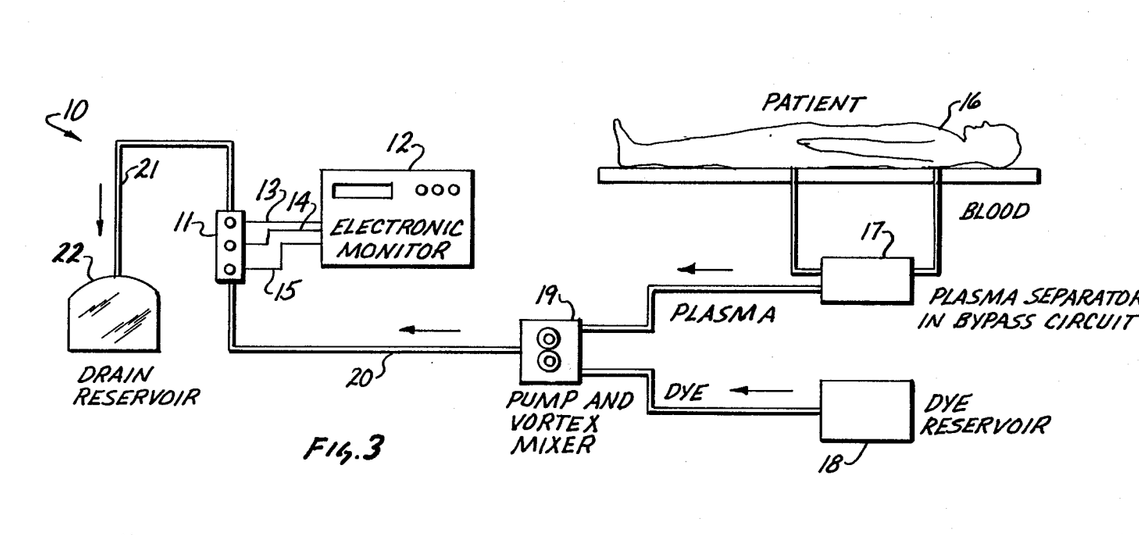
FIG. 3 is a diagrammatic view of the optical cuvette and associated components of the sampling station employed in the system.

Referring now to FIGS. 1–3 of the drawings, there is shown a system 10 (FIG. 3) constructed according to the invention for monitoring heparin concentration during extracorporeal bypass surgery that employs a sampling station 11 (FIGS. 1 and 2). Although the system 10 and sampling station 11 are designed for this particular application, various other arrangements may be employed within the inventive concepts disclosed.

As background for further description of the system 10 and sampling station 11, recall that azure A is a biological stain known for its metachromatic reaction with heparin. Heparin, an anionic polyelectrolyte, complexes with azure A, a basic dye, through its cationic groups. Three adsorption bands termed Alpha, Beta, and Mu bands, can be seen for the dye and heparin in dilute aqueous solutions. The Alpha band is that for the dye monomer in solution. The Beta band is that for the dye dimer, and the Mu band appears on adding heparin, and hence it is the metachromatic band.

Addition of heparin to the dye in solution decreases the Alpha and Beta bands characteristic of the dye and produces the Mu band at a shorter wavelength. This is attributed to the resonance in the dye molecules allowing a partial charge to form on each end of the dye dimer, and it permits loose interaction with the negatively charged heparin molecule to block electron delocalization. With less electron mobility, the dye molecule absorbs light energy at a shorter wavelength.

Metachromatic measurement of heparin was first employed in an extraction process, and it was thought that the metachromatic assays were not suitable for plasma heparin, mainly due to the interference of proteins and relatively high ionic strength. Klein used the method to determine plasma heparin and found it to be useful for heparin in the range of zero to ten units-per-mililiter (U/ml). He also found that the heparin concentrations determined with this assay are not exactly the same as those determined with coagulation assays. Sensitivity and reproducibility of the azure A assay was improved by using a less concentrated dye solution (0.001% as opposed to 0.01% or more) and monitoring the disappearance of dye absorption at 620 nanometers, the Alpha and Beta bands, as opposed to 520 nanometers, the Mu band.

In connection with the present invention, azure A measurement of heparin in bovine plasma was conducted to verify the methodology reported by Klein. A one-tenth percent (0.1%) azure A dye in deionized water was prepared as stock solution. For assays where heparin concentration ranged from zero to ten U/ml, two milliliters of 1:100 diluted stock dye plus one-tenth milliliter of plasma was mixed and read at 620 nanometers. For assays where heparin concentration ranged from zero to four U/ml, one milliliter of 8:100 diluted stock dye plus one milliliter of plasma was mixed and read at 620 nanometers.

The resulting measurements showed that elevated temperature decreases the test sensitivity. Small temperature deviations such as those observed at room temperature had negligible effect. Accordingly, the temperature effect on heparin measurement was ignored.

In addition, it was shown that within a physiological range (pH =5.9 to 7.0), no effect of pH was observed on the Azure A assay. As regards the effect of hemodilution on sensitivity, the sensitivity of the azure A assay was severely shifted from less sensitive to more sensitive as the hemodilution progressed. Tests were conducted to select a second wavelength to neutralize the effects of dilution. These tests indicated that the wavelength of 560 nanometers was effective.

As regards the effect on sensitivity of a different crystalloid solution as the hemodilutant, no difference was observed on the assay sensitivity between saline and plasmalyte as the hemodilutant. A for the effect of different heparins on sensitivity of azure A measurement, the USP unit was determined via sheep plasma coagulation assay and it was noted that for different heparins which rendered the same anticoagulation action, the azure A responses were quite different.

The effect of protamine titration on azure A measurement of heparin showed that protamine titrate responds to the macroanionic property of heparin just as azure A dye does, yet the affinity between protamine and heparin is stronger than the affinity between dye and heparin. In other words, protamine competes successfully with dye for heparin in a given system and the azure A assay can be used to quantitate heparin reversal with protamine.

In correlating the azure A measurements and the protopath measurement of different heparins, it was noted that the response of the azure A assay to the various types of heparin was different from the response of the protopath to these same heparins. It is understood that the azure A assay and protopath measure two different types of activities. According to the azure A assay, the measurement is more sensitive to beef lung heparin than porcine mucosa. The opposite is true with the protopath.

In summary, the in-vitro results on the azure A assay indicate that the azure A assay does measure heparin concentration, and it does measure protamine neutralization. In addition, it enables differentiation between heparin types and has the potential of enabling measurement of heparin potency towards the azure A.

The azure A assay can provide an accurate measurement of heparin. The effects of physiological parameters such as temperature, pH, crystalloid solution, and hemolysis are negligible. The major source of inaccuracy which this invention concerns is the effect of plasma dilution.

It is known that light transmittance through an azure A solution with added heparin is positively sensitive to heparin concentration (transmittance varies directly wit heparin concentration) for wavelengths in the region of 625 nanometers, relatively insensitive at wavelengths in the region of 530 nanometers, and negatively sensitive (transmittance varies inversely with heparin concentration) for wavelengths in the region of 505 nanometers. Based on this and the above considerations, the method of the invention includes taking transmittance measurements of the plasma at each of at least two different wavelengths, one of which is relatively insensitive to heparin dilution (and concentration), and comparing the measurements to neutralize the effect of dilution.

Considering now FIGS. 1–3 and the system 10 and sampling station 11 in further detail, the sampling station 11 is interconnected to an electronic monitor 12 by a diode line 13, a photodector line 14, and a common line 15 (FIGS. 1 and 3). Each of the lines 13–15 includes one or more electrically conductive lines that couple the sampling station 11 to the electronic monitor 12, and these components are used according to the invention to monitor the heparin concentration in blood plasma taken from a patient 16.

Blood from the patient 16 circulates through a bypass circuit 17 (FIG. 3) where the plasma is separated according to known techniques. A dye such as azure A from a dye reservoir 18 is mixed with the plasma in a pump and vortex mixer 19 (FIG. 3), and the resulting dye-containing plasma is conveyed through a conduit 20 to the sampling station 11 (FIGS. 1–3) where the heparin concentration is monitored by means of transmittance measurements taken in accordance with the invention. Finally, the dye-containing plasma is conveyed from the sampling station 11 through a conduit 21 to a drain reservoir 22 (FIG. 3).

The sampling station 11 includes an optical cuvette 23 (FIG. 2) that serves as vessel means for containing a sample of blood plasma to which a dye has been added. The vessel means may be a flow through housing through which blood flows continually or a container for holding a static blood sample. The optical cuvette 23 is substantially transparent to the light emitted by a diode light source 24 so that the light can pass through a sample of blood plasma within the optical cuvette 23 to a photodetector circuit 25 as indicated in FIG. 2 by an arrow 26 and an arrow 27.

The diode light source 24 serves as means for transmitting light at each of two different wavelengths through the sample while the sample is in the optical cuvette 2. This light is depicted by the arrow 26. The diode light source 24 employs known components and circuitry for this purpose, and it may include one or more light emitting diodes (not shown) that function to produce the light.

The photodector circuit 25 serves as means for detecting the light that is transmitted through the sample at each of the two different wavelengths to produce two different electrical signals, each one of which signals is indicative of the light transmitted through the sample at a respective one of the two different wavelengths. The light transmitted through the sample is depicted by the arrow 27. The photodetector circuit 25 employs known components and circuitry for this purpose, and it may include one or more photodetectors (not shown) that function to produce the two different electrical signals. These are coupled by the line 13 to the electronic monitor 12 for processing.

The electronic monitor 12 provides a signal processing function. It serves as means for processing at least one of the two different signals to determine the amount of heparin concentration and comparing the two different signals to compensate for the effect of plasma dilution. It employs known components and techniques to receive an electrical signal, and may include a microprocessor and digital readout (not shown).

Thus, the system 10 utilizes a dye such as azure A and a two wavelength approach to provide more accurate, convenient, and inexpensive monitoring, with continuous and immediate data availability.

Several design considerations are involved. A basic design consideration of the system is the measurement of light transmittances at 620 nanometers and 560 nanometers. Spectral scans of the sensitivity of the azure A assaying to heparin showed that the region of 610 nanometers to 640 nanometers provided sensitivity to heparin which was similar to that of the single 620 nanometers wavelength. This implied that light-emitting diodes with peak wavelengths of 630 nanometers (orange) could be utilized in this system. Similarly, light-emitting diodes with peak wavelengths at 560 nanometers (green) could also substitute for the single 560 nanometers wavelength.

Another design consideration is the measurement of transmittances rather than absorbances to correlate with heparin concentration. By definition, $A = -\log T$, where A is the absorbance and T is the transmittance. The only difference between the use of transmittances and absorbances is in the calibration curve relating these parameters to heparin. For example, the transmittance will increase with increased heparin concentration, whereas the absorbance will decrease with this same increase in heparin. Thus, the system 10 is described and claimed in terms of measuring transmittances, but it is intended that the scope of the invention as described and claimed include corresponding measurement of absorbances.

Figure 4:
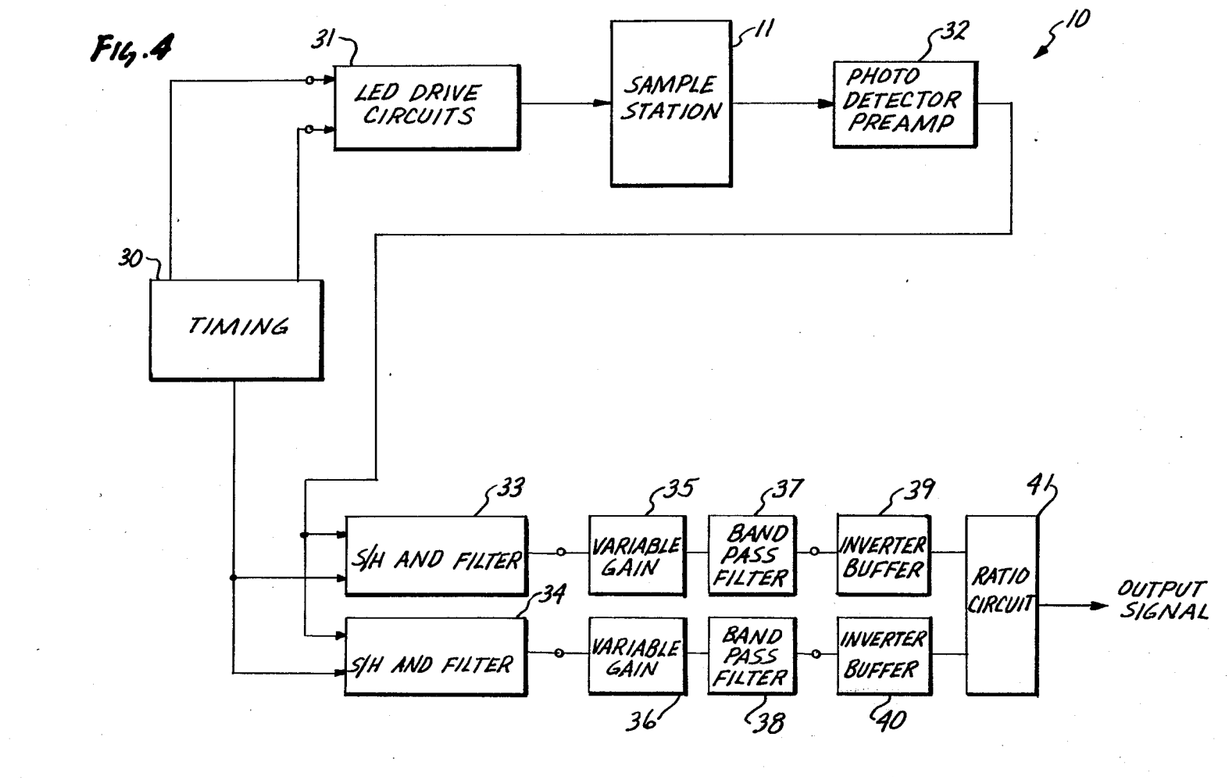
FIG. 4 is a schematic block diagram of signal producing and processing components of the system.

Considering now FIG. 4, there is shown a schematic block diagram of signal producing and processing components of the system 10. A timing circuit 30, which may employ a conventional microprocessor programmed according to known techniques together with supporting components provides timing signals for a drive circuit 31. The drive circuit 31 powers the diode light source 24 (FIG. 2) that is part of the sample station 11 (FIGS. 1–3), and the timing circuit 30 causes the diode light source 24 to be activated periodically to produce light at each of two different wavelengths (630 and 560 nanometers in the illustrated system 10). A system can be configured within the inventive concepts disclosed, however, that does not employ timing circuits.

Electrical signals from the photodectector circuit 25 of FIG. 2 are coupled from the sample station 11 to a photodetector preamplifier circuit 32 (FIG. 4) where the signals are filtered and amplified. The amplified output of the circuit 32 is coupled to a pair of sample-and-hold amplifiers 33 and 34 (FIG. 4) that are controlled by the timing circuit 30 so that they sample at the time the diode light source 24 is activated.

The output of each one of the sample-and-hold amplifiers 33 and 34 are processed in parallel according to known techniques using known circuitry, including a pair of amplifiers 35 and 36, a pair of bandpass filters 37 and 38, and a pair of inverter buffers 39 and 40 that serve as interfaces to a ratio circuit 41.

The output of the inverter buffers 39 and 40 are coupled to the ratio circuit 41. The ratio circuit 41 produces an OUTPUT SIGNAL that is indicative of the ratio of the outputs of the inverter buffers 39 and 40, and therefore the transmittances at each of the two different wavelengths. The OUTPUT SIGNAL maybe conventionally monitored with suitable separate equipment to provide a digital display indicative of the magnitude of the OUTPUT SIGNAL, and therefore the amount of heparin concentration. This may be done so that the system 10 displays the transmittances at each o the two different wavelengths, as well as the ratio of the transmittances, and the concentration of heparin as obtained from computations involving the ratio.

Figure 5:
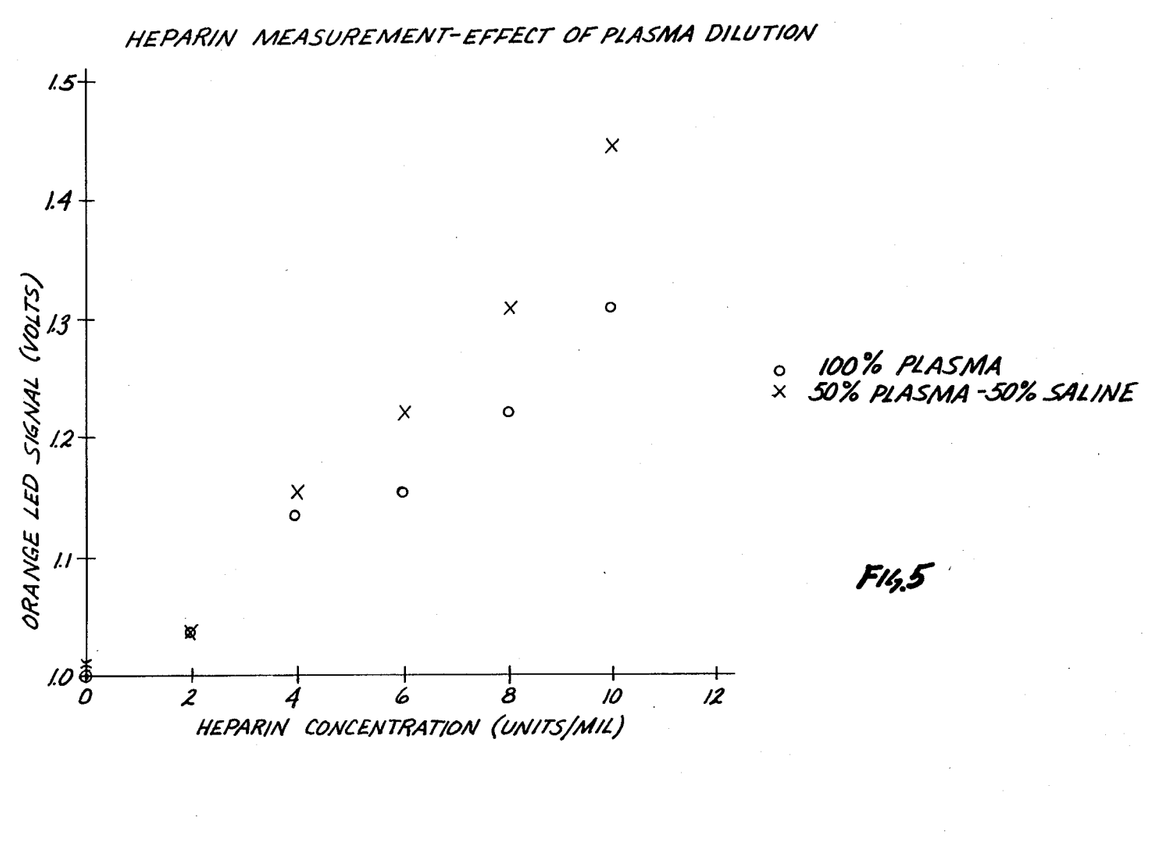
FIGS. 5–7 are plots showing the effect of plasma dilution on heparin measurement.
Figure 6:
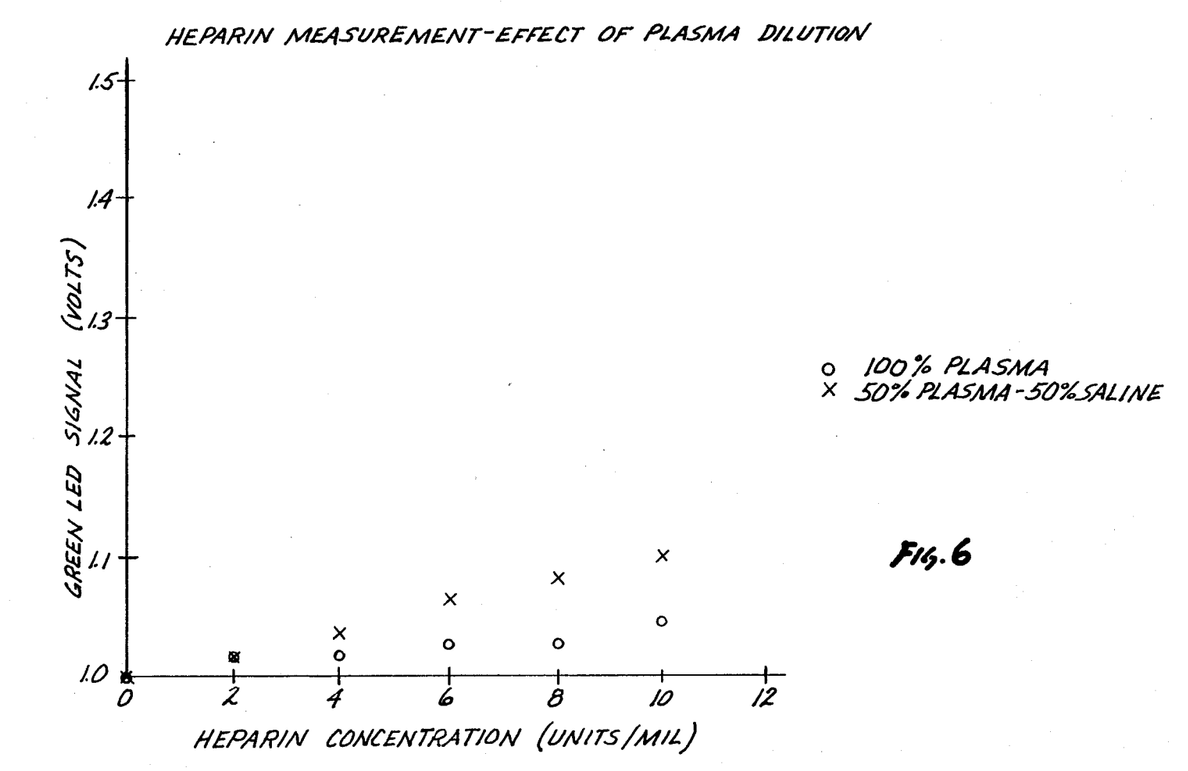

FIGS. 5–6 are three plots showing the effect of plasma dilution on heparin measurement. The orange LED signal or orange light has a wavelength or approximately 620 nanometers, while the green LED signal or green light has a wavelength of approximately 560 nanometers. FIG. 5 is a plot of measurements taken for the orange light for various values of heparin concentration, both with undiluted plasma (the "0's") and with fifty percent diluted plasma (the "X's").

Figure 7:
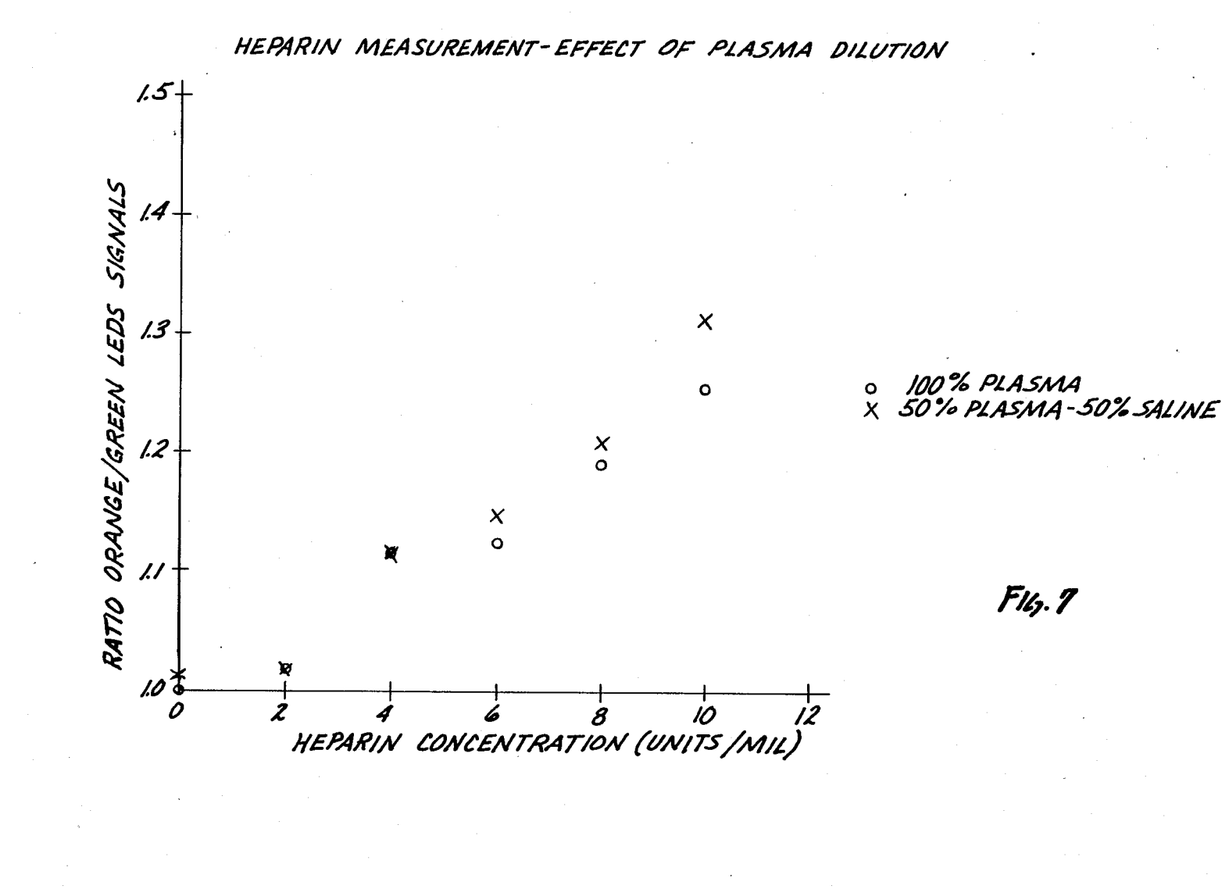

Similarly, FIG. 6 is a plot of measurements taken for the green light for various values of heparin concentration, both with undiluted plasma and with fifty percent diluted plasma, and FIG. 7 is a plot of the ratio of the orange and green light measurements.

Comparing the differences between the undiluted plasma and the fifty percent diluted plasma in the orange and green plots (FIGS. 5 and 6) as compared to the ratio plot (FIG. 7) shows that the difference is much smaller in the ratio plot. In other words, the dilution effect is much smaller.

It should be noted that signal comparison operations other than the described ratio operation may be performed on the measured signals to effect the neutralization of the plasma dilution on the measurement of heparin concentration. For example, the system of the invention may include suitable circuitry or programming to subject the two signals indicative of the measured wavelengths to an addition or power function operation in such a manner to negate the plasma dilution effect upon the heparin concentration measurement.

Thus, the overcomes various concerns of the prior art by identifying and using a second wavelength to obtain values that are compared with measurements taken with a first wavelength to minimize the effects of dilution. Although an exemplary embodiment of the invention has been shown and described, many changes, modifications, and substitutions may be made by one having ordinary skill in the art without necessarily departing from the spirit and scope of this invention.

What is claimed is:

1. A system for measuring heparin concentration in a sample of blood plasma, comprising:
   vessel means for containing a sample of blood plasma to which a dye has been added;
   light source means for transmitting light at two different wavelengths through the sample, a first of said wavelengths having a property of light transmittance through said sample which is dependent upon the concentration of heparin in said sample, with said second of said wavelengths having a property of light transmittance through said sample which is not dependent upon the concentration of heparin in the sample;
   detector means for selectively detecting the transmission of light passing through said sample at each of the two different wavelengths and producing two different signals indicative of the amount of light transmitting through the sample at each of said respective one of the two different wavelengths; and
   processing means for calculating a ratio of the two different signals to produce an output signal indicative of the amount of heparin concentration independent of plasma dilution.

2. A system as recited in claim 1, wherein:
   the vessel means is substantially transparent to the light at each of said two different wavelengths.

3. A system as recited in claim 1, wherein:
   the light source means includes at least one light emitting diode.

4. A system as recited in claim 1, wherein:
   the detector means includes at least one photodetector.

5. A system as recited in claim 1, wherein:
   the first wavelength is in the range of about 610 nanometers to about 640 nanometers; and
   the second wavelength is in the range of about 540 nanometers to about 560 nanometers.

6. A system as recited in claim 2, wherein:
   the first wavelength is in the range of about 610 nanometers to about 640 nanometers; and
   the second wavelength is on the range of about 520 nanometers to about 540 nanometers.

7. A method of measuring heparin concentration in a sample of blood plasma, comprising:
   containing a sample of blood plasma to which a dye has been added;
   transmitting light at two different wavelengths through the sample, a first of said wavelengths having a property of light transmittance through said sample which is dependent upon the concentration of heparin in said sample, with said second of said wavelengths having a property of light transmittance through said sample which is not dependent upon the concentration of heparin in the sample;
   detecting the amount of light transmitted through said sample at each of the two different wavelengths and producing two different signals, each one of which signals is indicative of the light transmitted through the sample at a respective one o the two wavelengths; and
   calculating a ratio of the two different signals to determine the amount of heparin in said sample independent of plasma dilution.

8. A method as recited in claim 7, wherein:
   the second one of the two wavelengths is chosen so that the amount of light of the second wavelength that is transmitted through the sample is substantially less dependent upon the amount of heparin dilution than is the amount of light of the first wavelength that is transmitted through the sample.

9. A method as recited in claim 8, wherein:
   the first wavelength is in the range of about 610 nanometers to about 640 nanometers; and
   the second wavelength is in the range of about 540 nanometers to about 560 nanometers.

10. A system as recited in claim 7, wherein:
    the second one of the two wavelengths is chosen so that the ratio of the amount of light of the first and second wavelengths that is transmitted through the sample various less with plasma dilution than does the amount of light of the first wavelengths that is transmitted through the sample.

11. A system as recited in claim 10, wherein:
    the first wavelength is in the range of about 610 nanometers to about 640 nanometers; and
    the second wavelength is on the range of about 520 nanometers to about 540 nanometers.

12. A method as recited in claim 7, wherein:
    the dye added to the sample is azure A.

13. A method as recited in claim 7, wherein:
    the first wavelength is on the range of about 610 nanometers to about 640 nanometers; and
    the second wavelength is in the range of about 480 nanometers to about 525 nanometers.

* * * * *

UNITED STATES PATENT AND TRADEMARK OFFICE
CERTIFICATE OF CORRECTION

PATENT NO. : 4,911,549
DATED : March 27, 1990
INVENTOR(S) : Maurice N. Karkar

It is certified that error appears in the above-identified patent and that said Letters Patent is hereby corrected as shown below:

Col. 1, Line 60, after "connected" delete "t" and insert -- to --

Col. 2, line 46, after "view" delete "f" and insert -- of --

Col. 6, line 48, after "each" delete "o" and insert -- of --

Col. 7, line 42, delete "transmitting" and insert -- transmitted --

Col. 8, line 25, after "one" delete "o" and insert -- of --

Signed and Sealed this

Sixteenth Day of June, 1992

*Attest:*

DOUGLAS B. COMER

*Attesting Officer*      *Acting Commissioner of Patents and Trademarks*